United States Patent
DeBoer et al.

(10) Patent No.: US 9,433,497 B2
(45) Date of Patent: Sep. 6, 2016

(54) SYSTEMS AND METHODS FOR CUSTOMIZING ADJUSTABLE INTRAOCULAR LENSES

(71) Applicants: Charles DeBoer, Pasadena, CA (US); Yu-Chong Tai, Pasadena, CA (US); Mark S. Humayun, Glendale, CA (US); Sean Caffey, Pasadena, CA (US)

(72) Inventors: Charles DeBoer, Pasadena, CA (US); Yu-Chong Tai, Pasadena, CA (US); Mark S. Humayun, Glendale, CA (US); Sean Caffey, Pasadena, CA (US)

(73) Assignee: 1Co, Inc., Pasadena, CA (US)

( * ) Notice: Subject to any disclaimer, the term of this patent is extended or adjusted under 35 U.S.C. 154(b) by 0 days.

(21) Appl. No.: 14/058,634

(22) Filed: Oct. 21, 2013

(65) Prior Publication Data
US 2014/0111765 A1    Apr. 24, 2014

Related U.S. Application Data

(60) Provisional application No. 61/716,152, filed on Oct. 19, 2012.

(51) Int. Cl.
*G02C 3/00* (2006.01)
*G02C 7/00* (2006.01)
(Continued)

(52) U.S. Cl.
CPC .......... *A61F 2/1618* (2013.01); *A61B 3/0025* (2013.01); *A61B 3/10* (2013.01); *A61B 3/09* (2013.01); *A61F 2/1624* (2013.01); *A61F 2240/002* (2013.01)

(58) Field of Classification Search
CPC ....... B29D 11/023; A61F 2/14; A61F 2/145; A61F 2/16; A61F 2/1602; A61F 2/1613; A61F 2/1616; A61F 2/1618; A61F 2/1621; A61F 2/1624; A61F 2/1627; A61F 2/1635; A61F 2/1637; A61F 2/1648; A61F 2/1659
USPC ........ 351/44, 159, 159.01–159.81, 178, 201, 351/203, 205, 206, 209, 211–214, 221, 246, 351/247; 623/6.11
See application file for complete search history.

(56) References Cited

U.S. PATENT DOCUMENTS

| 4,822,360 | A | 4/1989 | Deacon |
| 4,883,485 | A | 11/1989 | Patel |

(Continued)

FOREIGN PATENT DOCUMENTS

| EP | 1958592 A1 | 8/2008 |
| EP | 2221024 A1 | 8/2010 |

(Continued)

OTHER PUBLICATIONS

PCT International Application No. PCT/US2014/039792, Invitation to Pay Additional Fees and Partial Search Report mailed Sep. 19, 2014, 8 pages.

(Continued)

*Primary Examiner* — Mahidere Sahle
(74) *Attorney, Agent, or Firm* — Morgan, Lewis & Bockius LLP

(57) ABSTRACT

The lens geometry and power of an intraocular lens is optimized to provide both distance and near vision correction for a patient. The optimization may be based on one or more measured accommodation-related parameters and one or more estimated accommodation-related parameters. An accommodative amplitude may be predicted based on the measured and estimated accommodation-related parameters, and the optimized the intraocular lens geometry and power established based thereon.

24 Claims, 12 Drawing Sheets

(51) Int. Cl.
*G02C 7/02* (2006.01)
*A61F 2/16* (2006.01)
*A61B 3/10* (2006.01)
*A61B 3/00* (2006.01)
*A61B 3/09* (2006.01)

(56) References Cited

U.S. PATENT DOCUMENTS

| | | | |
|---|---|---|---|
| 4,902,293 | A | 2/1990 | Feaster |
| 5,554,187 | A | 9/1996 | Rizzo, III |
| 6,730,123 | B1 | 5/2004 | Klopotek |
| 7,438,723 | B2 | 10/2008 | Esch |
| 7,447,086 | B2 | 11/2008 | Wan et al. |
| 8,029,136 | B2 | 10/2011 | Dick et al. |
| 8,038,711 | B2 | 10/2011 | Clarke |
| 8,447,086 | B2 | 5/2013 | Hildebrand et al. |
| 8,603,164 | B2 | 12/2013 | Peyman |
| 2001/0049532 | A1 | 12/2001 | Saishin et al. |
| 2002/0055776 | A1 | 5/2002 | Juan, Jr. et al. |
| 2002/0161344 | A1 | 10/2002 | Peclat et al. |
| 2003/0083744 | A1 | 5/2003 | Khoury |
| 2004/0097957 | A1 | 5/2004 | Jaker et al. |
| 2004/0169816 | A1 | 9/2004 | Esch |
| 2004/0190153 | A1 | 9/2004 | Esch |
| 2005/0137703 | A1* | 6/2005 | Chen .................. 623/6.13 |
| 2006/0047339 | A1 | 3/2006 | Brown |
| 2007/0129800 | A1 | 6/2007 | Cumming |
| 2007/0142909 | A1 | 6/2007 | Peyman |
| 2008/0027460 | A1 | 1/2008 | Kobayashi |
| 2008/0114372 | A1 | 5/2008 | Edwards et al. |
| 2008/0319451 | A1 | 12/2008 | Zacharias |
| 2009/0043384 | A1 | 2/2009 | Niwa et al. |
| 2009/0240208 | A1 | 9/2009 | Cowan et al. |
| 2011/0270596 | A1 | 11/2011 | Weeber |
| 2012/0116506 | A1 | 5/2012 | Compertore |
| 2012/0296423 | A1 | 11/2012 | Caffey et al. |
| 2013/0035760 | A1* | 2/2013 | Portney .......... G02C 7/04 623/6.13 |
| 2013/0304203 | A1* | 11/2013 | Beer .................. 623/6.37 |
| 2013/0317607 | A1* | 11/2013 | DeBoer et al. .......... 623/6.13 |
| 2014/0358155 | A1 | 12/2014 | Deboer et al. |

FOREIGN PATENT DOCUMENTS

| | | |
|---|---|---|
| EP | 2709574 A2 | 3/2014 |
| GB | 1481427 | 7/1977 |
| WO | 92/17132 A1 | 10/1992 |
| WO | 2004/054471 A2 | 7/2004 |
| WO | 2010/035139 A2 | 4/2010 |
| WO | 2012/067994 A2 | 5/2012 |
| WO | 2012/158773 A2 | 11/2012 |
| WO | 2012/158773 A3 | 3/2013 |
| WO | 2014/063135 A2 | 4/2014 |
| WO | 2014/063135 A3 | 8/2014 |
| WO | 2014/193953 A2 | 12/2014 |
| WO | 2014/193953 A3 | 2/2015 |

OTHER PUBLICATIONS

PCT International Application No. PCT/US2013/041545, International Preliminary Report on Patentability mailed Dec. 4, 2014, 8 pages.

PCT International Application No. PCT/US2012/038102, International Preliminary Report on Patentability mailed Nov. 28, 2013, 13 pages.

PCT International Application No. PCT/US2012/038102, International Search Report and Written Opinion mailed Nov. 30, 2012, 17 pages.

PCT International Application No. PCT/US2013/041545, International Search Report mailed Aug. 19, 2013, 4 pages.

PCT International Application No. PCT/US2013/065858, International Search Report and Written Opinion mailed Jul. 2, 2014, 10 pages.

PCT International Patent Application No. PCT/US2013/065858, International Preliminary Report on Patentability mailed Apr. 30, 2015, 8 pages.

PCT International Patent Application No. PCT/US2014/039792, International Search Report and Written Opinion mailed Jan. 7, 2015, 23 pages.

* cited by examiner

SYSTEMS AND METHODS FOR CUSTOMIZING ADJUSTABLE INTRAOCULAR LENSES

CROSS-REFERENCE TO RELATED APPLICATIONS

This application claims priority to and the benefit of, and incorporates herein by reference in its entirety, U.S. Provisional Patent Application No. 61/716,152, which was filed on Oct. 19, 2012.

FIELD OF THE INVENTION

In various embodiments, the present invention relates generally to implantable intraocular lenses and, more specifically, to methods and systems for customizing implantable intraocular lenses for individual recipients.

BACKGROUND

The crystalline lens of the human eye refracts and focuses light onto the retina. Normally the lens is clear, but it can become opaque (i.e., when developing a cataract) due to aging, trauma, inflammation, metabolic or nutritional disorders, or radiation. While some lens opacities are small and require no treatment, others may be large enough to block significant fractions of light and obstruct vision.

Conventionally, cataract treatment involves surgically removing the opaque lens matrix from the lens capsule using, for example, phacoemulsification and/or a femtosecond laser through a small incision in the periphery of the patient's cornea. An artificial intraocular lens (IOL) can then be implanted in a lens capsule bag (the so-called "in-the-bag implantation") to replace the crystalline lens. Generally, IOLs are made of a foldable material, such as silicone or acrylics, for minimizing the incision size and required stitches and, as a result, the patient's recovery time. The most commonly used IOLs are single-element lenses (or monofocal IOLs, non-accommodating IOLs, non-focusing IOLs) that provide a single focal distance for distance vision. Typically, distance vision requires limited contraction of ciliary muscles in the eye (i.e., Emmetropia); thus monofocal IOL designs are relatively simple. For example, to choose an appropriate geometry for a monofocal lens having a desired focusing power, limiting factors of the eye's anatomy, such as the axial eye length and the power of the cornea, are taken into consideration. However, because the focal distance is not adjustable following implantation of the monofocal IOL, patients implanted with monofocal IOLs can no longer focus on objects at a close distance (e.g., less than twenty-five centimeters); this results in poor visual acuity at close distances.

Recently, accommodating intraocular lenses (AIOLs) have been developed to provide adjustable focal distances (or accommodations) relying on the natural focusing ability of the eye. Because an AIOL works closely in coordination with the eye tissue, the focusing power thereof is sensitive to the geometric properties of the eye tissue. For example, ciliary muscles of the eye may contract, causing a change in the diameter and/or the shape of the lens capsule accommodating the AIOL; this results in an adjustment of the focal distance. Additionally, the shorter the focal distance of the AIOL, the more sensitive the AIOL will be to a change in geometry of the eye tissue. Because the anatomic geometry of the human eye may change with age and behavior, and geometric variances exist among people, it remains challenging to determine an appropriate geometry of the AIOL for each specific patient to satisfy her unique needs.

Consequently, there is a need for methods and systems for determining an AIOL geometry that can provide a high degree of accommodation and desired focusing power for a given individual.

SUMMARY

In various embodiments, the present invention relates to systems and methods for determining the geometry of an AIOL for providing a desired focusing power and accommodation level customized to the patient. In one implementation, the anatomic geometry specific to the patient's eye is measured using any of various techniques. In addition, some patient-specific geometric properties of the ocular tissue may be estimated based on, for example, characteristics of the patient, statistical data, and/or one or more statistical models. The optimal configuration of the AIOL may be predicted/estimated based on directly measured properties (i.e., the patient's ocular geometry and the amount of optical correction needed for normal vision) and indirectly obtained and/or estimated properties (e.g., based on statistics). The geometry and optical properties of the AIOL can then be calculated based on the optimized accommodation power and the necessary level of vision correction.

In particular, characteristics of the lens may be optimized based on the patient's accommodative capabilities, which are estimated based on direct and indirect factors as expalined above. For example, the lens curvature, fill level and the refractive properties of the fill medium can be varied, while still providing proper far-field correction, to maximize the focusing range of the AIOL that the patient will experience given his accommodative capabilities. The more robust those accommodative capabilities, the less it will be necessary to vary the lens properties. Finally, the in situ optical performance of the lens can be predicted using a conventional mathematical lens model. As a result, the AIOL is optimized for a patient's most probable accommodation capabilities while providing sufficient optical correction for long-distance vision.

Thus, for example, an initial baseline level of lens curvature (the base power) may be established in a conventional fashion to achieve correction of the patient's far-field vision. Depending on the patient's accommodative capacity, the lens power may be varied. For example, suppose it is estimated that a patient has two diopters of accommodation. The lens power of the lens may then be increased by two diopters, resulting in two diopters of additional lens power that translate into additional distance of focusing capability.

The optimized lens characteristics may be used to manufacture a customized lens or, more commonly in a clinical setting, to select an optimal lens from a set of variously sized lenses. The geometry and optical properties of the selected AIOL, may be altered by adjusting the volume and/or optical properties of the fluid medium contained therein. Because patient-specific geometries are evaluated and considered prior to or during AIOL implantation, the current invention provides an AIOL with the appropriate focusing power and optimized accommodation properties for a given patient.

The term "indirectly obtained" means obtained in a manner other than direct measurement, e.g., based on statistics, correlations or averages. The terms "accommodation," "accommodation power," and "accommodative amplitude" herein refer both to the eye's ability to adjust its optical power to focus on an object at various distances, and to the capacity of a lens in accordance herewith to change its optical properties in response to the eye's accommodation mechanism; these terms are used interchangeably. In addition, the terms "optical power," "focusing power," "lens power," and "refractive power" are also used herein interchangeably.

Accordingly, in one aspect, the invention pertains to a method for customizing an intraocular lens geometry and power to provide both distance and near vision correction for a patient. In various embodiments, the method includes determining a baseline amount of far-field focal correction for the patient; measuring one or more accommodation-related parameters for the patient; estimating one or more accommodation-related parameters for the patient based at least in part on statistical data; predicting an accommodative amplitude based on the measured and estimated accommodation-related parameters; and determining the intraocular lens geometry and power based at least in part on the baseline correction and the predicted accommodative amplitude. In one embodiment, the method further includes choosing an optimal lens from among multiple differently sized lenses based on the determined geometry and power. In another embodiment, the method includes manufacturing an intraocular lens based on the determined geometry.

The measured accommodation-related parameter(s) may be one or more of corneal topography, corneal keratometry, corneal aberration, axial eye length, anatomic geometry of the natural lens and or lens capsule including lens or lens capsule volume, diameter, thickness, or curvature, geometry of ciliary muscles in a relaxed and contracted position, or the position of the lens and lens capsule relative to the eye. The estimated accommodation-related parameter(s) may include a demographic characteristic, a behavioral characteristic, and/or a medical history. In one implementation, the intraocular lens geometry and power is further determined based on a mathematical model.

In various embodiments, the method includes adjusting the volume and/or the optical property of the fluid contained in the intraocular lens for maximizing the working focal range of the lens. In some embodiments, the method includes the steps of predicting an accommodated lens power; and selecting a base power of the intraocular lens based at least in part on the difference between the predicted accommodated lens power and the predicted accommodative amplitude. Additionally, the base power and the accommodative amplitude may be set to ensure that the intraocular lens encompasses both distance vision and near vision.

In some embodiments, the method further includes estimating (i) the force applied to the intraocular lens by a lens capsule based on the measured and estimated accommodation-related parameters, (ii) the pressure inside the intraocular lens, and (iii) one or more parameters relating to a shell of the intraocular lens; and predicting the accommodative amplitude based at least in part on the estimated force, pressure, and/or parameter(s) relating to the shell. Additionally, the accommodative amplitude may be further determined based on a mathematical model.

In another aspect, the invention relates to a system for customizing an intraocular lens geometry and power to provide both distance and near vision correction for a patient. In various embodiments, the system includes a measuring system for (a) determining a baseline amount of far-field focal correction for the patient and (b) measuring one or more accommodation-related parameters for the patient; a memory for storing a database having accommodation-related statistical data; and a processor in operative communication with the measuring system and the memory. In some embodiments, the processor is configured to estimate one or more accommodation-related parameters for the patient based at least in part on statistical data; predict an accommodative amplitude based on the measured and estimated accommodation-related parameters; and determine the intraocular lens geometry and power based at least in part on the baseline correction and the predicted accommodative amplitude. In one implementation, the processor is further configured to choose an optimal lens from among multiple differently sized lenses based on the determined geometry and power. In another implementation, the processor is configured to communicate with a manufacturing system for manufacturing the intraocular lens based on the determined geometry and power. Additionally, the processor may be configured to determine the intraocular lens geometry and power based on a mathematical model.

The measuring system may include a keratometer, a wavefront aberrometer, an IOL Master, a corneal topographer, ultrasound or optical coherence tomography, a Scheimpflug camera, a magnetic resonance imaging device, a computed tomography device and/or an intraoperative aberrometer. The measuring system may measure one or more of corneal topography, corneal keratometry, corneal aberration, axial eye length, anatomic geometry of the natural lens and or lens capsule including lens or lens capsule volume, diameter, thickness, or curvature, geometry of ciliary muscles in a relaxed and contracted position, and the position of the lens or lens capsule relative to the eye. In addition, the database may store statistical data on a demographic characteristic, a behavioral characteristic and/or a medical history.

In various embodiments, the processor is configured to compute an adjustment to the volume and/or the optical property of the fluid contained in the intraocular lens for optimizing distance and near vision correction. In some embodiments, the processor is further configured to predict an accommodated lens power and predict a base power of the intraocular lens based at least in part on the difference between the predicted accommodated lens power and the predicted accommodative amplitude. Additionally, the processor may be further configured to set the base power and the accommodative amplitude to ensure that the intraocular lens encompasses both distance vision and near vision.

The processor may be configured to estimate (i) a force applied to the intraocular lens by a lens capsule based on the measured and estimated accommodation-related parameters, (ii) the pressure inside the intraocular lens, and (iii) one or more parameters relating to a shell of the intraocular lens; and predict the accommodative amplitude based at least in part on the estimated force, pressure, and/or parameter(s) relating to the shell. Additionally, the processor may be configured to determine the accommodative amplitude based on a mathematical model.

Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, routines, steps, or characteristics may be combined in any suitable manner in one or more examples of the technology. The terms "substantially" and "approximately" mean±10% and, in some embodiments, within ±5%. The headings provided herein are for convenience only and are not intended to limit or interpret the scope or meaning of the claimed technology.

BRIEF DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which.

DETAILED DESCRIPTION

Figure 1A:
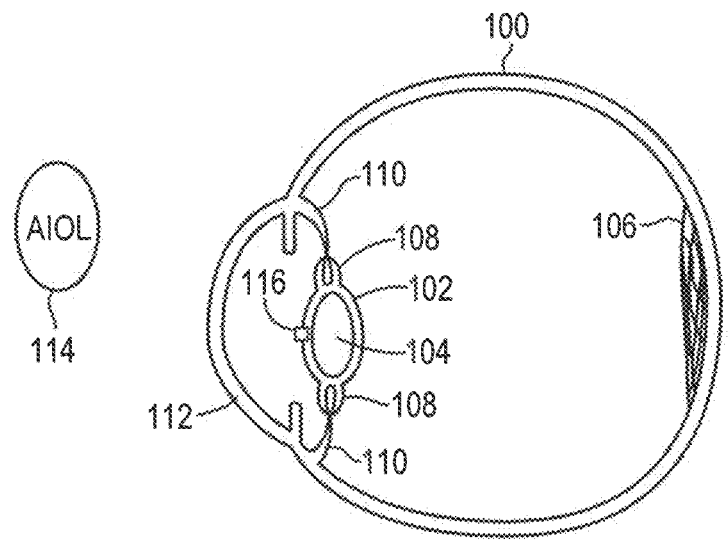
FIGS. 1A and 1B depict sectional side views, respectively, of a human eye and an AIOL in accordance with an embodiment of the invention.
Figure 1B:
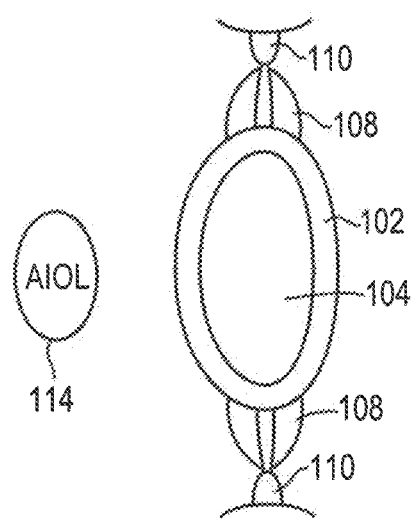
Figure 1C:
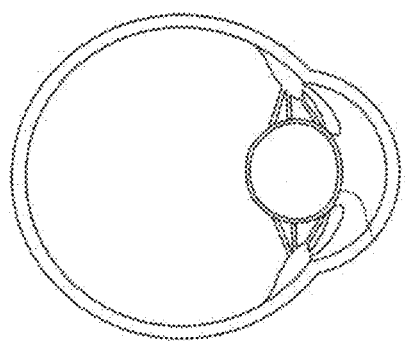
FIGS. 1C and 1D depict an eye in an accommodated state and an unaccommodated state, respectively.
Figure 1D:
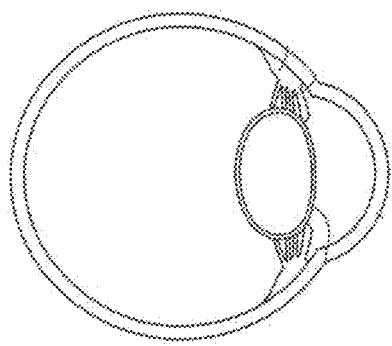

Refer first to FIGS. 1A 1D, which illustrate a structure and operation of a human eye 100. The eye 100 has a lens capsule 102 with a crystalline lens 104 that focuses light onto the retina 106; the lens capsule 102 is joined by ligament fibers (or zonules) 108 around its circumference to ciliary muscles 110, which are further attached to the inner surface of the eye 100. Contractions of the ciliary muscles 110 release tension on the lens capsule 102, thereby causing the lens 104 to bulge outward and reduce its radius of curvature (FIG. 1C). Consequently, the optical power of the lens 104 increases; this is an accommodated state suitable for short-distance vision. Similarly, referring to FIG. 1D, when the ciliary muscles 110 relax, the lens 104 is pulled into a flattened form by the lens capsule and zonules. The flattened lens 104 provides the base focusing power for long-distance vision.

Figure 2A:
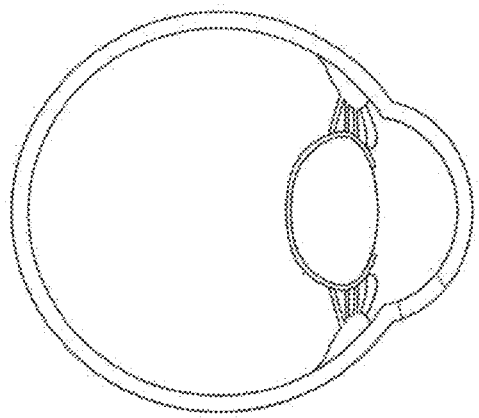
FIGS. 2A and 2B depict an eye having a capsulotomy and a peripheral capsulotomy, respectively.
Figure 2B:
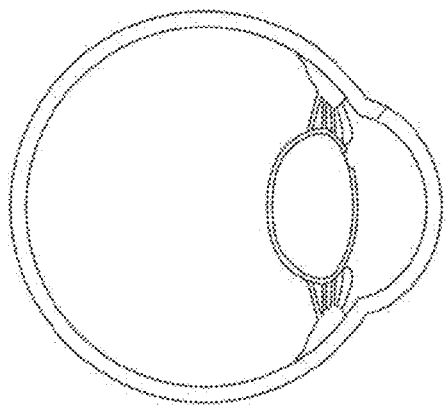
Figure 2C:
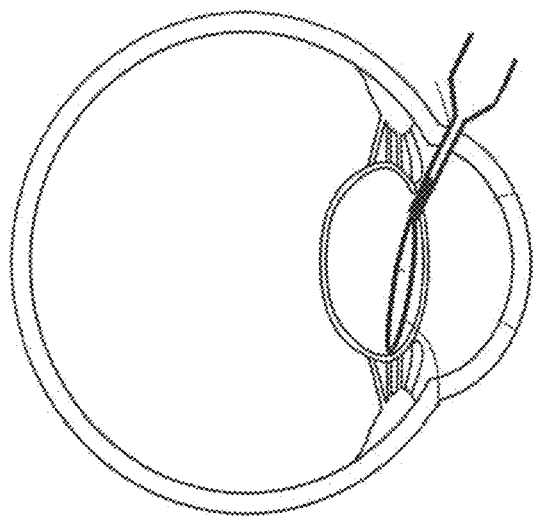
FIG. 2C illustrates an AIOL being inserted into the eye in accordance with an embodiment of the invention.

Referring to FIGS. 2A and 2B, during cataract surgery, lens 104 is removed from the lens capsule 102 using, for example, phacoemulsification and/or a femtosecond laser through a small incision in the periphery of the patient's cornea 112. An AIOL 114 shaped and sized as further described below is inserted through a small incision on the anterior capsule portion 116 (i.e., central capsulotomy, FIG. 2A) or periphery of the patient's cornea 112 (i.e., peripheral capsulotomy, FIG. 2B) into the lens capsule 102. Note that the lens capsule is less able to directly exert force on the lens to mold the lens if a large aperture is opened along the anterior surface of the lens. The surgeon then ensures that the AIOL 114 is deployed and placed correctly and that there are no tears in the capsule 102. Referring to FIG. 2C, in various embodiments of the present invention, the AIOL 114 includes an outer IOL shell and a medium in the space enclosed therewithin; in some embodiments, the AIOL 114 further includes an internal optic to increase the accommodation and generate an appropriate focusing power; see, e.g., U.S. Ser. No. 13/350,612, filed on Jan. 13, 2012, and Ser. No. 13/896,539, filed on May, 17, 2013; the entire disclosures of both of these applications are hereby incorporated by reference. The accommodation of the AIOL 114 can be effectively altered by varying the shape of the outer IOL shell, the volume and refractive index of the filling medium, and/or the shape and refractive index of the internal optic. For example, adjusting the amount of liquid medium contained in the AIOL 114 may change the shape and/or optical properties (such as optical power) of the lens; and changing refractive properties (e.g., the refractive index) of the fluid inside the lens may change the refractive power of the lens. In some embodiments, the liquid medium is a liquid, gel, gas, or a curable polymer that can be cured after implantation of the liquid filled lens. Because the liquid medium may be introduced into the AIOL 114 via, for example, a refill valve, the volume and material constituting the medium may be adjusted either during the initial AIOL implantation or at a later time.

Figure 3:
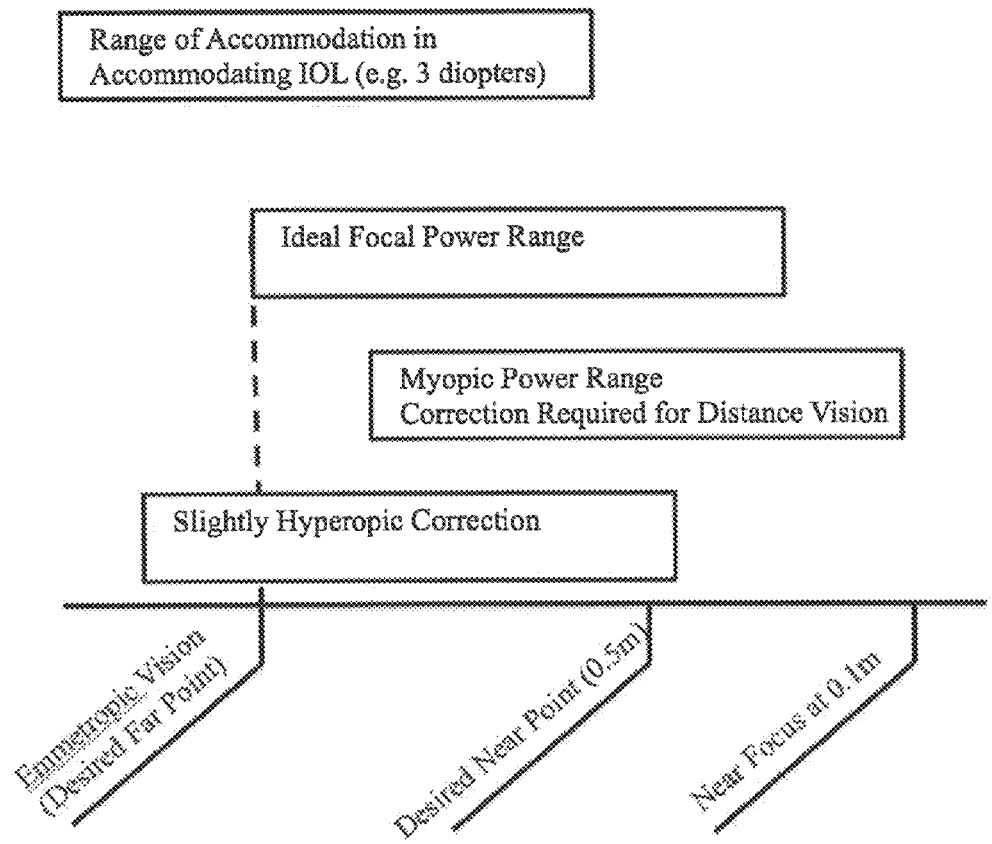
FIG. 3 depicts an AIOL having adjustable focus lengths in accordance with an embodiment of the invention.

Referring to FIG. 3, the AIOL 114 may provide a range of focal lengths. For example, the AIOL 114 may focus at infinity (or a far point) when it is completely unaccommodated (thereby providing emmetropic vision) and may focus on a near point (e.g., between 0.5 to 0.1 meter away, such as approximately 0.33 meter away) during maximum accommodation (e.g., approximately 3 diopters of accommodation). In one embodiment, the AIOL 114 is implanted to provide slightly hyperopic vision such that both the far and near focal points can be realized by accommodation of the lens (and adjustments of the geometry and/or optical properties of the AIOL 114 such that the performance thereof is sufficiently close to the ideal, desired performance). This is known as a slightly hyperopic correction. In this correction regime, the difference between the actual and ideal vision at long distances may be kept sufficiently small to avoid clinically significant vision problems. In particular, if the difference is small enough, correction will be tolerated well by the patient. Therefore, in contrast to monofocal IOLs where the focal length is made to be somewhat short (i.e., myopic), for the focus-changing AIOL 114, a slightly hyperopic design may allow the lens to be adjusted through the full range of focal lengths needed for normal vision, including focal lengths for long distance vision as well as short distance vision.

In various embodiments, the geometric and optical properties of the AIOL 114 are determined and/or adjusted based on the natural geometry of the patient's eye, which is measured prior to or during the AIOL implantation. For example, the axial eye length and power of the cornea may be measured to aid in calculating the ideal base power of the AIOL 114 and/or determining any shape changes needed to correct for higher-order aberration errors, such as astigmatism. In various embodiments, the base power of the AIOL is chosen to approximate the base power of an emmetropic outcome; the focusing power of the AIOL is then given by adding the expected accommodative amplitude to the emmetropic base power. As used herein, the term "base power" refers to the power of the lens when the ciliary muscles are relaxed and the lens is pulled to a flattened form by the zonules and lens capsule; this is the lowest power of the lens and corresponds to long distance vision. To provide the AIOL 114 with accommodation (i.e., adjustable focal lengths), the AIOL 114 may rely on dynamic interactions with the natural anatomy of the eye tissue (e.g., lens capsule 102, ciliary muscles 110 and zonules (not shown)). For example, the tension that the lens capsule 102 applies to the AIOL 114 due to relaxation of the ciliary muscles 110 may change the geometry (and therefore the focusing power) of the AIOL 114. Additionally, the amount of ciliary muscle contraction and the effects thereof on the surrounding ocular geometry may change the position and shape (and thereby the geometric and optical performance) of the AIOL 114, which may, in turn, change the base power and/or affect the expected and actual accommodation levels of the AIOLs 114. As a result, in some embodiments, additional patient-specific geometric parameters of the eye (e.g., the size, diameter, thickness, or curvature of the lens capsule 102, the size and/or the volume of the nature lens 104, the diameter of the ciliary muscles in the contracted and non-contracted states, the motion of the ciliary muscles, the depth of the anterior chamber, the shape and thickness of the cornea, corneal keratometry, corneal aberration, the geometry of the eye, such as length and strength, of the zonules, and/or the expected position of the AIOL 114 relative to the eye) are measured and considered when designing or choosing the geometry of the AIOL 114 to provide a desired accommodation level and focusing power. In this way, the AIOL 114 may provide adjustable focal distances in a manner similar to the natural human lens—i.e., relying on interactions with the natural anatomy of the eye tissue.

In various embodiments, the AIOL 114 is sized and shaped to conform to the geometry of the eye (e.g., fitting within the lens capsule 102); this ensures the patient's comfort after the AIOL implantation. Additionally, because geometric conformity may affect the accommodation level that the AIOL 114 undergoes, the measured geometric data of the natural lens, and other patient-specific data (both measured and estimated, as described below) may be used to optimize the lens so that it will focus through as much distance as possible given the patient's inherent accommodation capacity. As a result, in one implementation, the base power is calculated in a conventional fashion based on the correction needed for far-field vision, and the predicted accommodation capacities of the patient are used to optimize the AIOL 114. Alternatively, the base power may be determined based on the expected power of the AIOL in the accommodated state minus the expected accommodation power of the AIOL. Thus, if the AIOL 114 is molded in the accommodated form, prediction of the accommodation power of the AIOL may be necessary to determine the base power of the AIOL, thereby achieving good distance vision after implantation.

Any conventional techniques and measuring systems may be used alone or in combination to measure the natural and implanted lens geometry—i.e., to establish parameters that may be directly measured. These techniques include, but are not limited to, a keratometer, a wavefront aberrometer, an IOL Master, a corneal topographer, ultrasound imaging (e.g., ultrasound biomicroscopy (UBM)), optical coherence tomography (OCT), a Scheimpflug camera, magnetic resonance imaging (MRI), computed tomography (CT), an intra-operative aberrometer, or a custom tool inserted into the eye during surgery. For example, the ultrasound imaging or OCT may measure the axial eye length; corneal topography, a keratometer, an autorefractor, or an IOL master may measure the power of the cornea. Particular techniques may not be suitable in all circumstances. For example, ultrasound imaging or OCT may be used to measure lens thickness reliably, but measuring lens diameter accurately with these techniques may be challenging, as the lens is visually blocked by the iris, and an ultrasound measurement from side to side of the lens is difficult to take. The lens diameter, however, may be acquired based on the lens thickness, which is measurable, and the known relationship between the lens thickness and diameter.

The geometry of the human eye, like the rest of the body, varies naturally among people; these anatomic variations may result from, for example, characteristics such as ethnicity, genetic, or environmental factors. Additionally, it is well known that the human eye changes geometric and optical properties throughout life (e.g., due to aging). For example, the human eye grows substantially after birth, and thereafter throughout life; this causes changes in the position as well as the size of the lens. Further, medications and certain lifestyle choices can influence the eye's responsiveness and ability to focus; for example, steroid (e.g., prednisone) and chemotherapy agent medications can negatively affect the eye's accommodative capacities, as can excessive attention to electronic displays (e.g., television, videogames, computer screens, etc.). These factors, although relevant on a population-statistical level and not a patient-specific level, nonetheless can contribute to an accurate estimate of the patient's accommodative capabilities. Accordingly, in one embodiment, patient-specific anatomic parameters are estimated based on statistical data relating to characteristics (including lifestyle choices and medications) of the patient prior to designing or implanting the AIOL 104. This indirect data may then be used in conjunction with the directly measurable quantities as described above to derive the properties of the AIOL 104 that optimize focal range.

Statistically useful patient characteristics may include demographic characteristics (such as age, sex, educational background, origin, or ethnicity), behavioral characteristics (such as number of daily hours spent watching electronic displays), the patient's medical history, and other characteristics that may affect the geometric and optical properties of the human eye. For example, contraction of the ciliary muscles is known to relate to the patient's accommodative amplitude; larger ciliary muscles may cause a larger accommodation response. See, e.g., Burd et al., "Numerical modeling of the accommodating lens," *Vision Res*, vol. 42, pp. 2235-251, August 2002 (the entire disclosure of which is hereby incorporated by reference). As a result, the expected accommodation may be determined by measuring the total motion of the ciliary muscles. In one embodiment, a patient with a smaller range of muscle motion is considered to have a smaller accommodative amplitude than a patient with a larger ciliary muscle motion. Pupillary constriction can be used as an indirect indicator of ciliary motion, as the pupil has parasympathetic innervation. Therefore, a large pupillary constriction may indirectly indicate an adequate ciliary muscle motion in the absence of other findings. Additionally, the mass of the ciliary muscles and the total contractile force of the ciliary muscles may deteriorate with a patient's age; this results in a decrease in the accommodative amplitude due to aging. Likewise, the zonules may become weaker with the age, thereby becoming less capable of transmitting the accommodative amplitude to the implanted intraocular lens.

Accordingly, the statistical model may include any models and analyses that relate patient characteristics to the geometric and optical properties of the eye. For example, the statistical models may predict that the eye's accommodative amplitude positively correlates with the range of motion of the patient's ciliary muscles, which may be detected directly and measured; the size of the natural lens; and/or the ratio of the pupil size in a constricted state to a dilated state. The eye's accommodative amplitude negatively correlates with the patient's age and/or daily time spent watching electronic displays. Additionally, statistics may correlate steroid treatments with a reduction in accommodative amplitude. In some embodiments, a statistical model may be used to empirically predict the probability of a patient's eye having certain geometric and optical properties at a certain age and/or the probability of having geometric variances in certain years. Relevant statistical data are readily available and a suitable statistical model may be created without undue experimentation. For example, different statistical factors may be weighted differently based on the strength of a particular factor in influencing accommodative capacity and/or patient characteristics. For example, for a patient more than sixty-five years old, tissue changes due to aging may be given the most weight in the statistical model, whereas the same factor may be de-emphasized for young patients. Statistics for factors such as steroid medication may already be based on dosage, providing an implicit weighting. By combining direct measurements with these indirect parameters, the accommodation power of a patient's eye may be estimated more accurately, thereby allowing the geometry of the AIOL 114 to be optimized for the patient's needs.

Figure 4:
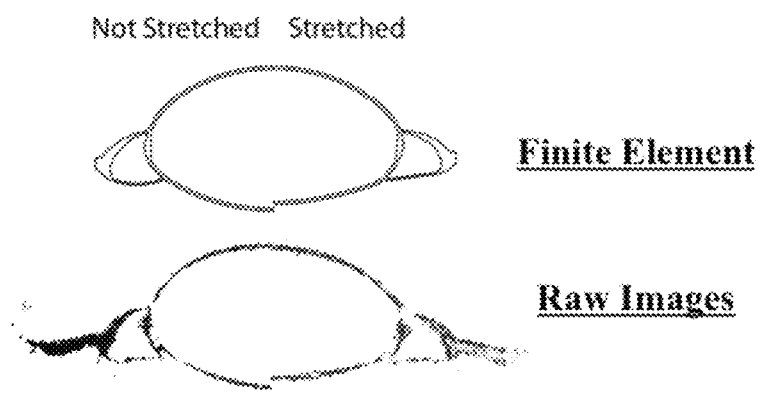
FIG. 4 depicts a mathematical model with finite element analysis for predicting AIOL performance in accordance with an embodiment of the invention.

In certain embodiments, the directly measured and/or indirectly obtained ocular properties are used in conjunction with a mathematical lens model to predict lens power, accommodative amplitudes, base power, and/or optical aberrations when the AIOL 114 is implanted in the patient's eye. The optical properties of the AIOLs 114 of different shapes and sizes may then be simulated in the patient using this mathematical lens model. The AIOL 114 with the best simulated optical performance may be chosen from a set of discrete lenses. In some embodiments, the mathematical lens model is utilized to adjust the AIOL geometry to optimally interact with the patient's ocular tissue. The mathematical modeling may be established based on, for example, a regression analysis of the anatomic data that is obtained using any of the measuring techniques or systems described above, lens data, and/or patient-specific data as described above. In a simplest example, the cornea and AIOL 114 are simulated as compound lenses; the focusing power thereof is then given as:

$$\text{Power} = \frac{1}{f_{cornea}} + \frac{1}{f_{AIOL}} - \frac{d}{f_{cornea} f_{AIOL}},$$

where $$\frac{1}{f_{cornea}}$$

is the measured power of the cornea, $f_{AIOL}$ is the focal length of the AIOL 114 (i.e., the distance between the center of the AIOL 114 and the retina 106), and d is the distance between the centers of the cornea and the AIOL 114. Additionally, by comparing the diameters and/or lengths of the ciliary muscles in the contracted and non-contracted states, the tension that causes the AIOL 114 to bulge outward may be estimated. Based on the material properties of the AIOL 114, the change in the radius of curvature may then be estimated. As a result, the accommodation of the AIOL 114 may be approximated as:

$$Accom = \frac{n_{lens} - n_{media}}{n_{media}} \left[ \frac{1}{\Delta R_1} - \frac{1}{\Delta R_2} \right],$$

where $n_{media}$ and $n_{lens}$ are the refractive indices of the surrounding medium and AIOL, respectively, and $\Delta R_1$ and $\Delta R_2$ are changes of the curvatures of the anterior lens surface and posterior lens surface of the AIOL, respectively. Alternatively, lens performance may be simulated using finite element, ray tracing, or other modeling techniques. Referring to FIG. 4, a mathematical model with finite element analysis may be used to predict lens performance. For long-distance vision, the lens capsule needs to pull the anterior and posterior surfaces of the AIOL tightly. If the AIOL is too small for the lens capsule (e.g., containing too little fluid), the anterior and posterior surfaces of the lens may remain in the accommodated state and cannot be effectively extended into a flattened form. Likewise, if the lens is too big (e.g., containing too much fluid), the lens capsule may not be able to shape the AIOL into the flattened state. As a result, even when the ciliary muscles relax, the AIOL may retain its accommodated state.

The mathematical lens model may include geometric properties of the lens for predicting the optical performance thereof. An AIOL that has the same or slightly larger thickness (e.g., less than two times thicker) and a smaller radius of curvature compared with that of the natural lens in the emmetropic position may have a larger accommodative power compared to a smaller sized AIOL. This is because the steeper anterior curvature is more easily deformed to a flattened shape when the zonules exert tension on the lens. This steepened shape needs to be thick enough for the natural lens capsule to effectively compress the anterior and posterior portions of the lens. Therefore, if the AIOL is too small, the zonules may not be able to transmit force to the lens capsule and cause deformation of the intraocular lens. Accordingly, the AIOL may remain in an accommodated or near-accommodated state after implantation. If, however, the AIOL is two times thicker than the natural lens, the AIOL is expected to accommodate less due to a geometric inability of the ciliary muscles and zonules to effectively transmit force to the intraocular lens and deform it. Similar work has been performed on the natural human lens, where certain researches have indicated that an increase in lens thickness relates to a repositioning of the lens relative to the other ocular structures and inefficient accommodation. See, e.g., Cook et al., "Aging of the human crystalline lens and anterior segment," *Vision Res*, vol. 34, pp. 2945-54, November 1994 (the entire disclosure of which is hereby incorporated by reference).

Further, the mathematical lens model may determine the optical power and accommodative amplitude based on the dimensions of the lens relative to the surrounding lens capsule. This may be critical for an intraocular lens that mimics the natural lens, or fills out the lens capsule. A closer and more conformal fit to the natural lens capsule size allows the ciliary muscles to transmit forces more effectively to the capsule and lens. For example, a geometric theory of presbyopia holds that a loss of accommodative amplitude with age results from the growth of the lens with age. As the lens becomes larger, the geometric position of the lens prevents the ciliary muscles and zonules from effectively transmitting forces to change the lens shape. In a similar manner, an AIOL lens that mimics the natural anatomy of the eye is sized appropriately to harness the accommodative amplitude of the ciliary muscles. A too-large AIOL lens may not be compatible with the natural focusing mechanism of the eye.

In various embodiments, the optical properties of the AIOLs 114 of different shapes and sizes are simulated in the patient using a mathematical lens model. The AIOL 114 with the best simulated optical performance (i.e., producing the best match to the desired focusing power and accommodation power) may then be chosen from a set of discrete lenses. To optimize the match between the real optical performance of the AIOL 114 and the desired ideal performance, the geometry of the AIOL 114 and/or the volume and/or refractive properties of the filling medium may also be adjusted. In one implementation, this adjustment is first simulated using the mathematical lens model. In some embodiments, the patient-optimized geometry of the AIOL 114 is derived by inserting the parameters, including the desired focusing power and accommodation level and the directly measured and indirectly obtained geometric and optical properties of the ocular tissue, into the mathematical lens model. Based on the obtained ideal geometry, the AIOL 114 is then custom manufactured using any conventional IOL manufacturing system.

Figure 5:
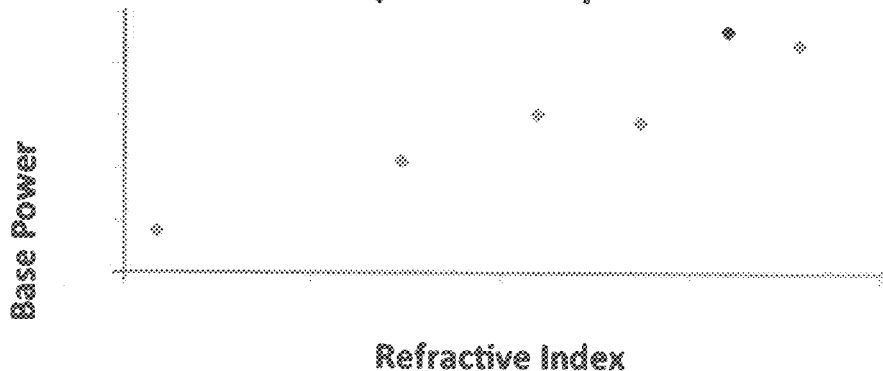
FIG. 5 illustrates the relationship between lens power and refractive index of the filling fluid for a particular AIOL in accordance with an embodiment of the invention.
Figure 6A:
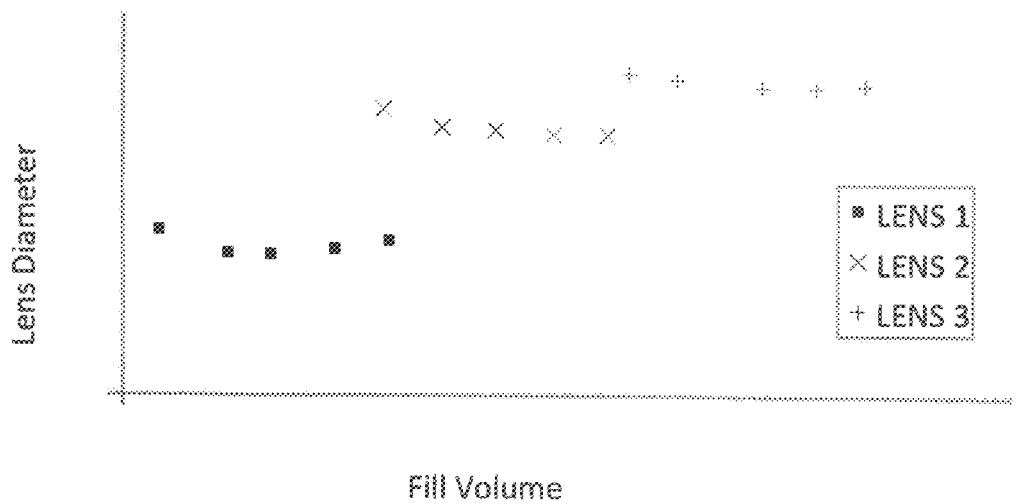
FIGS. 6A-6D depict relationships between the spatial dimensions of a lens and a volume of filling fluid for various AIOLs in accordance with various embodiments of the invention.
Figure 6B:
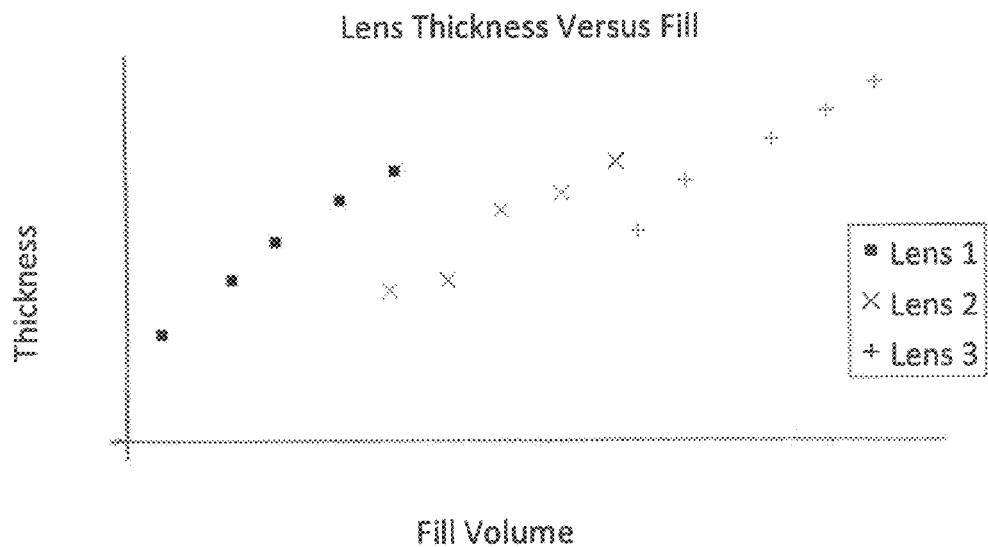
Figure 6C:
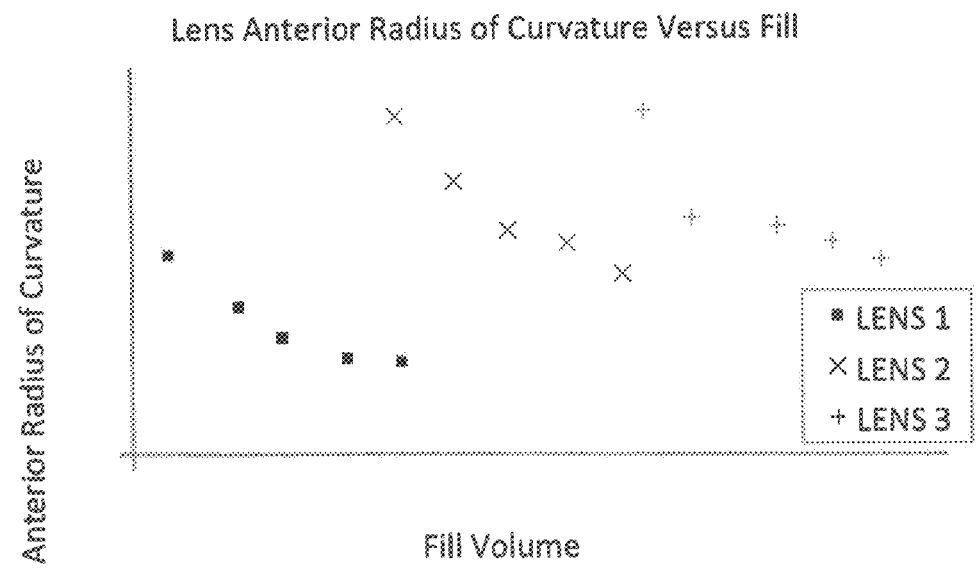
Figure 6D:
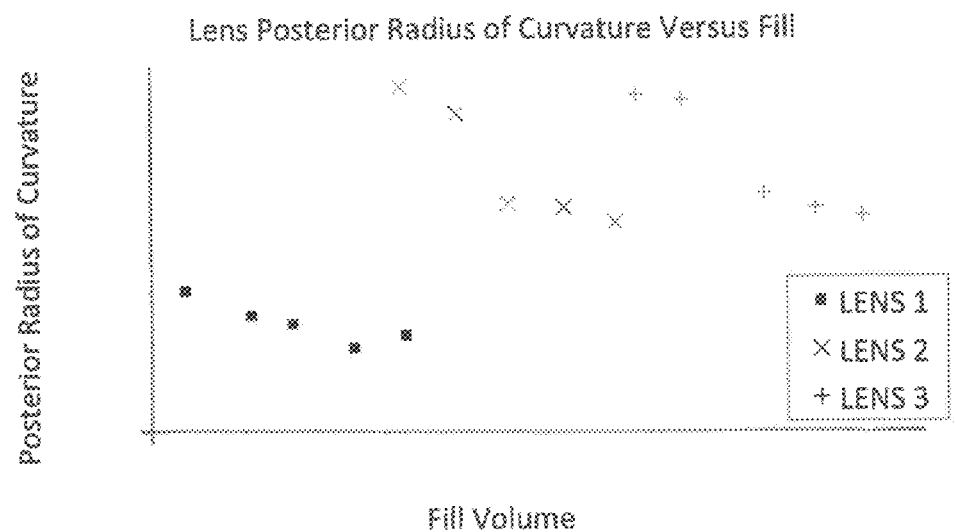
Figure 6E:
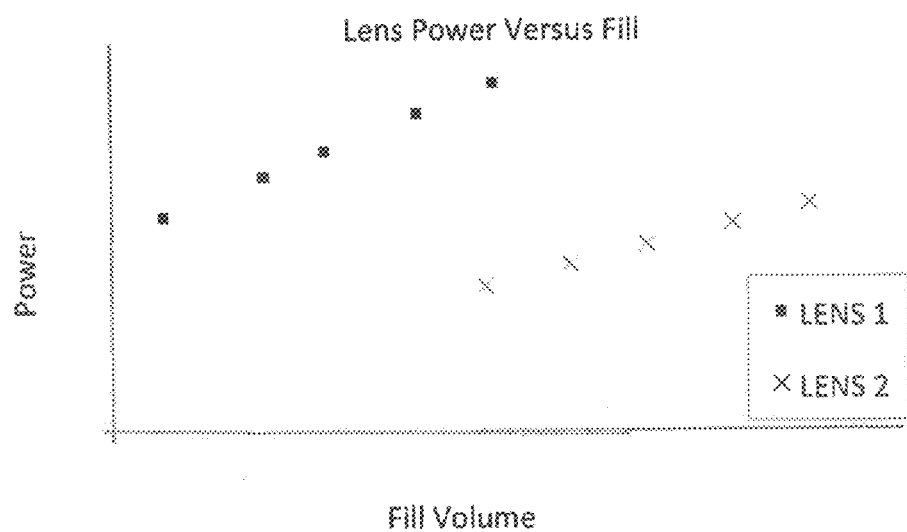
FIG. 6E depicts the relationship between optical power and volume of filling fluid for various AIOLs in accordance with various embodiments of the invention.

Optical properties, such as focusing power, of the AIOL 114 may be altered after implantation or during the implantation process. In certain embodiments, the AIOL 114 is implanted and the optical parameters of the lens are tuned during implantation, e.g., in response to patient feedback or by viewing a retinal image in real time while making adjustments of the AIOL 114. For example, the AIOL 114 may be adjusted while the ciliary muscles are relaxed. In various embodiments, to cause the ciliary muscles to relax (cycloplegia) during AIOL adjustments, pharmacological relaxation of the muscles may be performed. Pharmacological cycloplegia agents may include muscarinic antagonists, such as topical tropicamide, atropine, cyclopentolate, homatropine, and scopolamine. Preferably the pharmacologic agent is short-acting to prevent residual cycloplegia after the procedure. In one implementation, long-distance vision may be induced by providing a visual cue to the ipsilateral, contralateral, or both eyes. Additionally or alternatively, the patient may be asked to fixate on a target at a certain distance for inducing long-distance vision. In some embodiments, the AIOL 114 is adjusted in a follow-up visit after implantation. Post-implantation optical adjustments may include, for example, focusing power adjustment, accommodation level adjustment, and/or astigmatic and higher order aberrational adjustment. In one embodiment, the base power of the AIOL is adjusted by tuning the refractive index of the filling fluid (FIG. 5).

FIGS. 6A-6E depict the dimensions, as a function of fill volume, of three exemplary lenses manufactured from different lens molds. The lenses are designed to undergo small changes in diameter with fill volume—that is, each lens has a specific and distinct diameter, which remains nearly constant over a range of filling volume. Therefore, it is possible to choose an intraocular lens with a diameter closely matched to the patient's specific geometry such as the diameter of the natural lens. Because lens thickness increases with the amount of lens fill, the amount of fill may be adjusted to optimize accommodation of the lens in the natural lens capsule. As an example, the lens thickness in the accommodated state may be chosen to be 25% thicker than the natural lens. Additionally, the anterior and posterior radii of curvature of the lens decrease with the fill amount, thereby yielding a larger focusing power (assuming the filling liquid has a constant refractive index).

Figure 7A:
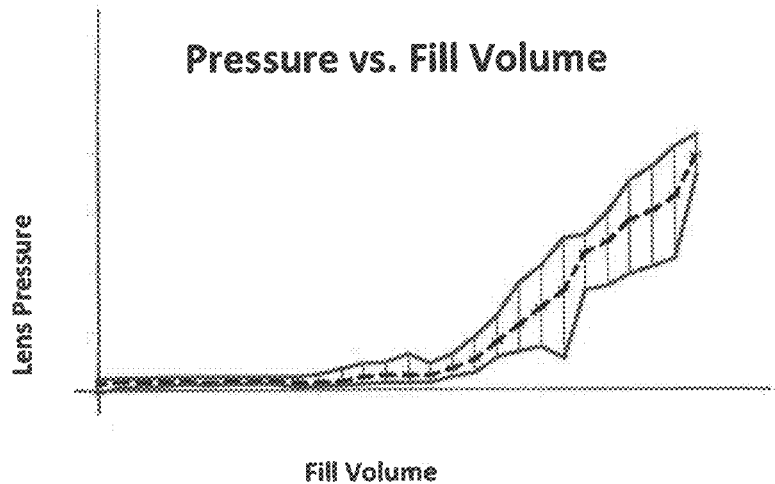
FIG. 7A depicts the relationship between lens pressure and volume of filling fluid for various AIOLs in accordance with various embodiments of the invention.

Referring to FIG. 7A, in some embodiments, accommodation of the AIOL depends on the lens pressure (i.e., the pressure that the filling fluid exerts on the lens wall) that may increase with the amount of filling fluid. The lens pressure is relatively low before the AIOL is inflated. During filling, the lens wall starts to stretch and/or expand; as a result, the internal pressure of the AIOL increases with the fill amount (assuming the internal volume of the AIOL is isovolumetric). The higher the pressure, the more difficult it is to mold the inflated AIOL. The relationship between the lens pressure and a wall tension may be described using Laplace's law.

$$\Delta p = \gamma \left( \frac{1}{R_1} + \frac{1}{R_2} \right)$$

where $\Delta p$ is the pressure across the lens wall, $R_1$ and $R_2$ are the curvatures of the anterior lens surface and posterior lens surface of the AWL, respectively, and $\gamma$ is a wall tension. The wall tension may depend on the design of the AIOL, such as the thickness and elastic modulus of the wall. Accordingly, variations in lens pressure may alter the wall tension and the shape of the which, in turn, changes the accommodation power.

Figure 7B:
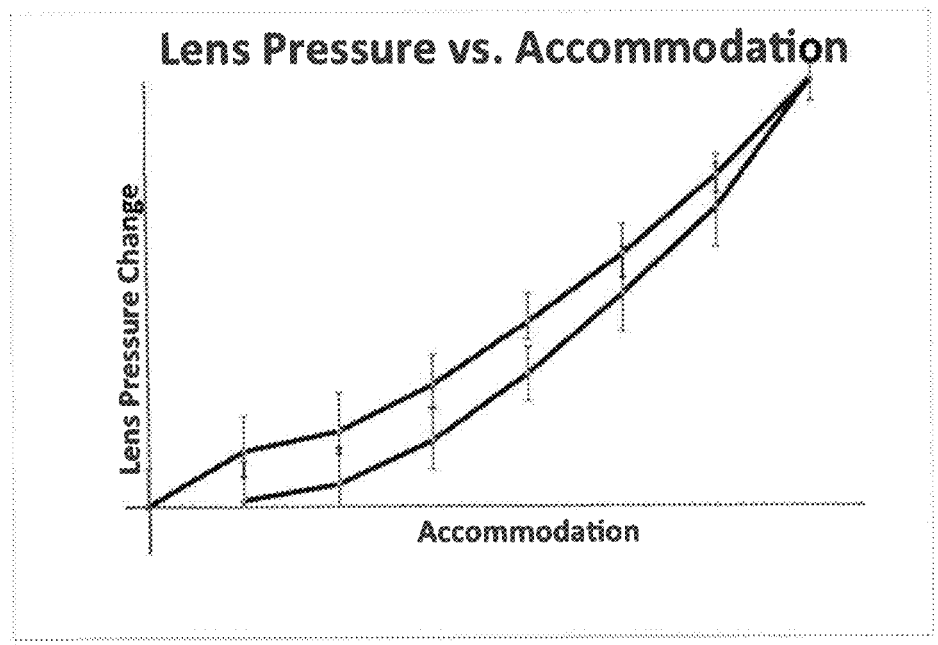
FIG. 7B depicts a relationship between lens pressure and accommodation amplitude of AIOLs in accordance with various embodiments of the invention.

With reference to FIG. 7B, in some embodiments, the lens pressure correlates with the accommodation amplitude. For example, the higher the lens pressure, the more accommodated/stretched the AIOL will be. The exact amount of lens pressure for accommodating a certain number of diopters depends on the amount and properties of the filling fluid in the AIOL. For example, when the lens is filled to a high level, the lens pressure is high; as a result, a substantial force is required to mold the AIOL from the accommodated state to the unaccommodated state. This force may depend on the movement of the ciliary muscle, the ability of the zonules and other patient-specific geometric and anatomic parameters that affect the interaction between the AIOL and the lens capsule.

Figure 7C:
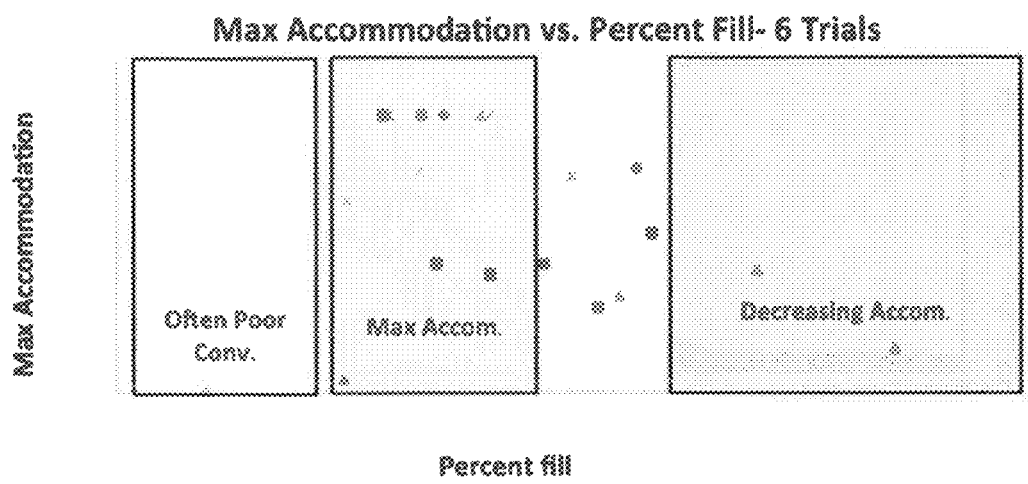
FIG. 7C depicts a relationship between accommodation amplitude and volume of filling fluid for various AIOLs in accordance with various embodiments of the invention.

When the lens pressure is so high that the lens capsule is incapable of shaping the lens, the accommodative amplitude may decrease. FIG. 7C illustrates how lower filling volumes may produce high levels of accommodation. Additionally, when insufficient pressure is available at low filling volumes, there may be no accommodation because the AIOL may no longer interact with the surrounding lens capsule. Thus, in certain embodiments, the lens is matched to patient-specific parameters by monitoring lens pressure during or after lens filling. This pressure can then determine the expected lens performance and optimal filling level.

Figure 8:
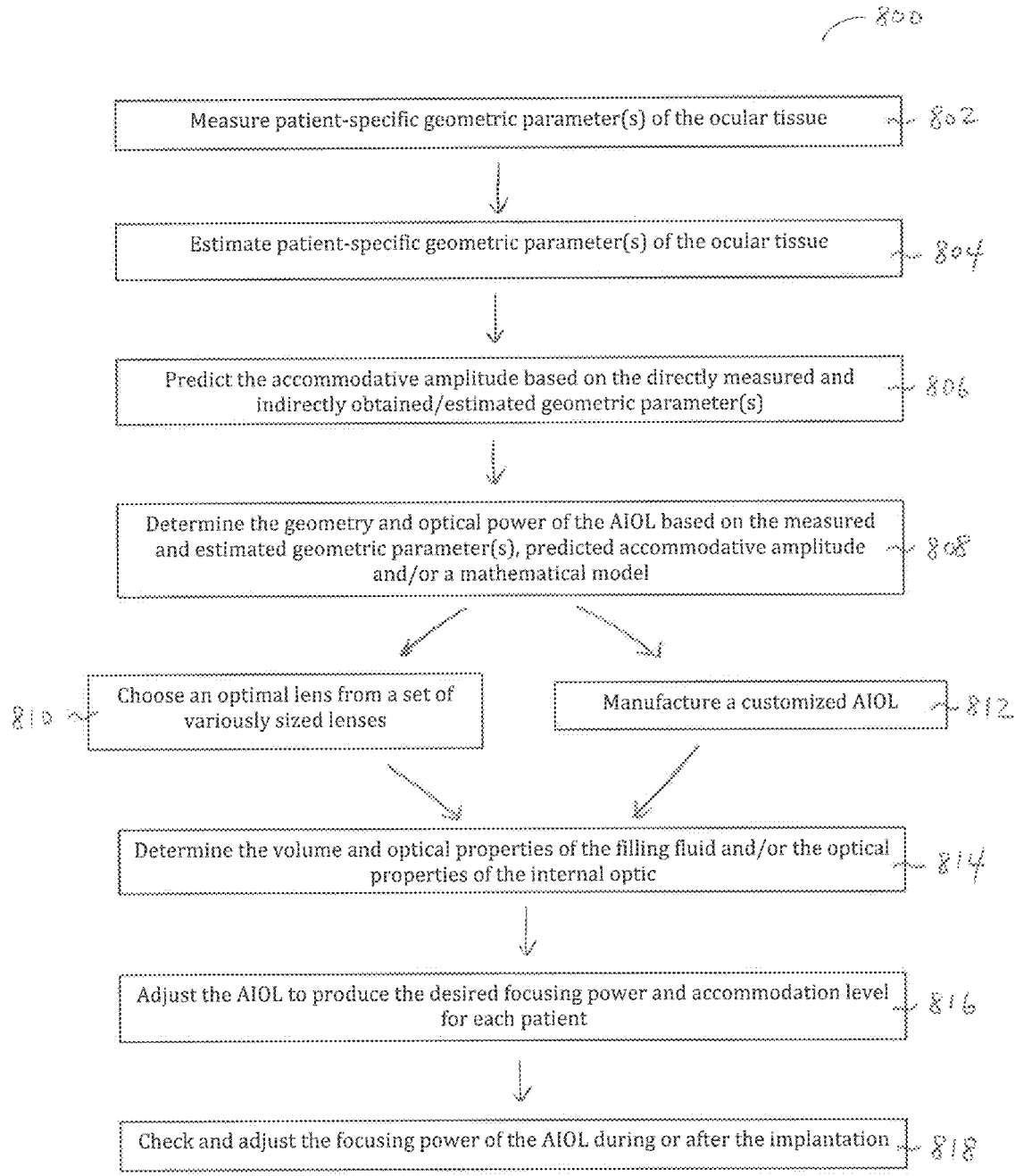
FIG. 8 depicts a method for determining an intraocular lens geometry and power in accordance with embodiments of the current invention.

A representative method 800 for determining the AIOL geometry and optical power to provide both distance and near vision correction for a patient in accordance with embodiments of the current invention is shown in FIG. 8. In a first step 802, one or more patient-specific geometric parameters of the ocular tissue are directly measured. In a second step 804, one or more patient-specific geometric parameters of the ocular tissue are indirectly obtained/estimated using statistical data relating to patient characteristics and/or a statistical model relating the statistical data to geometric parameters applicable to the patient. In a third step 806, the accommodative amplitude is estimated/predicted based on the directly measured and indirectly obtained and/or estimated patient-specific geometric parameters. In a fourth step 808, the geometry and optical power of the AIOL 114 are determined based on the measured and estimated patient-specific geometric parameters, the predicted accommodative amplitude, and a mathematical lens model. The determined geometry is used to choose an optimal lens from a set of variously sized lenses (that are determined by their original molded states) (in a fifth step 810) or to manufacture a customized AIOL (in a sixth step 812); this way, the selected/manufactured lense may be optimized for a patient's most probable accommodation power and have the optical performance (e.g., focusing power) that can satisfy the patient's needs (and best match the natural lens capsule geometry).

In an exemplary design, the AIOL 114 is a fluid-filled lens (as described, for example, in the '612 and '539 applications); the fine adjustment used to match the optical performance of the chosen/manufactured AIOL to the desired value is achieved by adjusting the fluid volume and optical properties (e.g., refractive index) of the filling fluid and/or the optical properties of the internal optic. Accordingly, in a seventh step 814, the desired fluid volume and optical properties of the filling fluid and/or the optical properties of the internal optic are determined based on patient characteristics, anatomic data that is directly measured and indirectly obtained/estimated, and/or a mathematical lens model. In a eighth step 816, the AIOL 114 is adjusted based on the parameters obtained in the sixth step to produce the desired focusing power and accommodation level for each patient. In addition, higher-order aberrations may be corrected by adjusting the lens design. In various embodiments, during or after the implantation, the focusing power and accommodation of the AIOL 114 may be checked and adjusted using an intraoperative aberrometer (as described in the '612 application, for example), projecting an image on the retina, or asking the patient for visual feedback (in an ninth step 818).

For example, suppose that the motion of a 45-year-old patient's ciliary muscles is first measured using UBM and determined to have a 1-millimeter change when looking between near and far distances. The natural lens thickness is measured using ultrasound imaging and found to be 4 millimeters thick. The anterior chamber depth is 3 millimeters. Additionally, the patient has no history of steroid medication, so no correction of accommodative amplitude is necessary. Using this data, the approximate lens volume is estimated to be 140 microliters based on the lens thickness and patient's age (alternatively, this may be determined using MRI). The desired base power for an emmetropic outcome is 20 diopters. The predicted accommodative amplitude is 4.5 diopters computed based on the patient's age, expected anterior and posterior curvatures of the lens chosen relative to the natural lens, no corrections resulting from steroid use, and a 1 millimeter change in ciliary muscle diameter in response to accommodative stimulus. A lens power of 24.5 (i.e., 20+4.5) diopters in the accommodated state is then chosen for the patient. The natural lens diameter is estimated from the lens thickness, patient's age, and ethnicity as 10 millimeters (this may also be obtained with MRI). The chosen intraocular lens has a diameter of 9.8 millimeters at a fill level of 123 microliters, which corresponds to 24.5 diopters. Using the chosen lens, a more accurate estimate of the accommodative amplitude is computed, and the fill level is further adjusted to be 121 microliters. In addition, a mathematical lens model may simulate the geometric properties of the chosen lens at the determined fill (i.e., 121 microliters) inside the lens capsule. For example, the model may demonstrate that the thickness of the AIOL at this fill is 4.5 millimeters. Since the expected anterior chamber depth with the surgical incision in the lens capsule is 2.8 millimeters, the geometry of the lens is acceptable.

In another example, a 56-year-old patient having a natural lens diameter of 9.7 millimeters, lens thickness of 3.9 millimeters is provided with an AIOL having a 4.8 millimeter thickness in the accommodated state and a lens diameter of 7.1 millimeters. The resulting accommodation is determined to be 4.2 diopters. Likewise, a patient of the same age having a natural lens thickness of 3.8 millimeters and a diameter of 8.9 millimeters produces a 6.2 diopter maximum accommodation. Both patients' eyes are implanted with similar capsulotomies; the power of the AIOL expected to produce 6.2 diopters is 2 diopters stronger than the AIOL producing 4.2 diopters. In addition, by using an alternate mold, with a closer match to the diameter of the natural lens (all other parameters being equal), or preferentially filling the lens to a larger diameter, a higher accommodative amplitude is expected from the AIOL in the first patient. The focusing power may then be adjusted to achieve emmetropic vision for the first patient.

Figure 9:
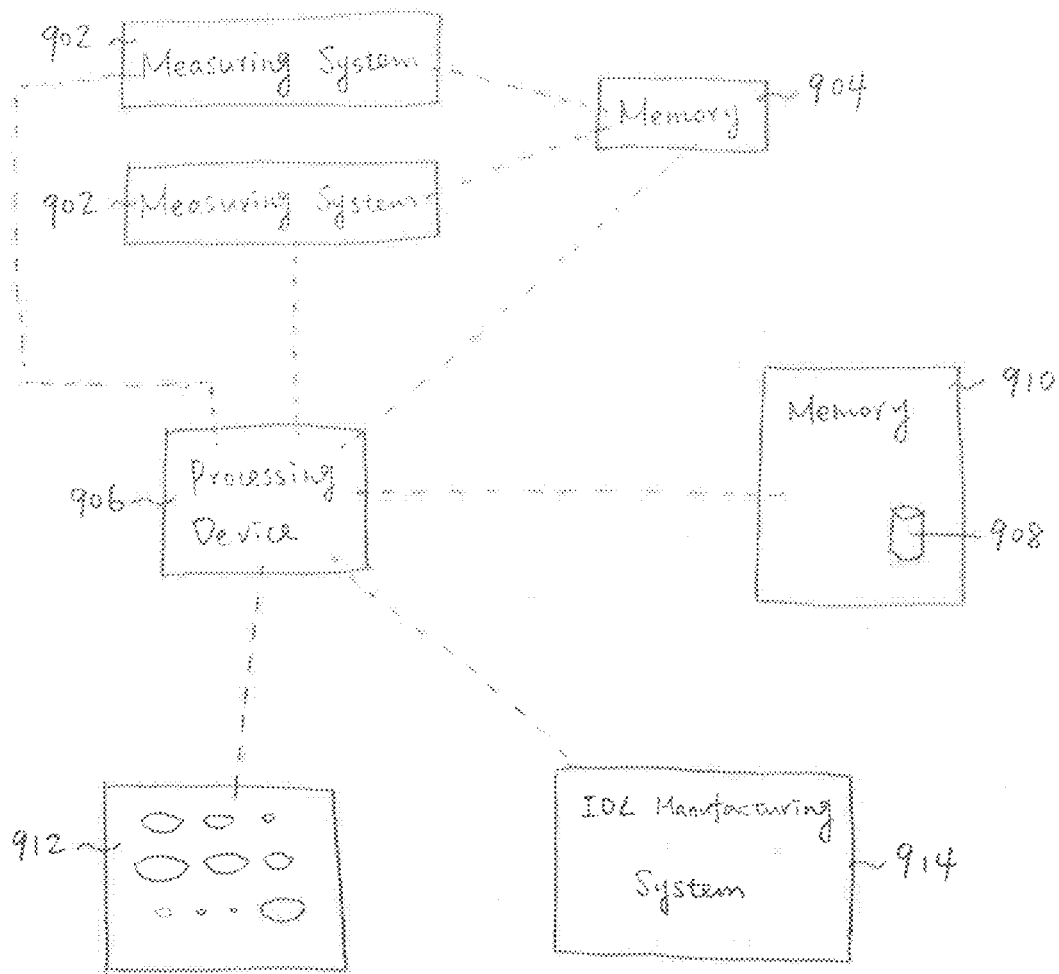
FIG. 9 depicts a system for determining an intraocular lens geometry and power in accordance with embodiments of the current invention.

A system 900 for determining the AIOL geometry and optical power to provide both distance and near vision correction for a patient in accordance with embodiments of the current invention is shown in FIG. 9. The system 900 includes one or more measuring systems 902 for measuring patient-specific geometric parameters of the eye anatomy. The measured data is stored in a memory 904 internal or external to the measuring system(s) 902. In addition, the system 900 includes a processing device 906 that can access a database 908 stored in a memory 910 to retrieve statistical data related to patient characteristics. The memory 910 may be the same or different from the memory 904 and may be internal or external to the processing device 906. The processing device 906 can then estimate patient-specific geometric parameters based on the statistical data and, in some embodiments, one or more statistical models. Subsequently, the processing device 906 accesses the memory 904 to acquire the measured geometric data, thereby predicting the accommodative amplitude of the eye based on the measured geometric parameters stored therein and the patient-specific geometric parameters previously estimated. The processing device 906 may then calculate the geometry and optical power of the AIOL based on the measured and estimated patient-specific geometric parameters, the predicted accommodative amplitude, and a mathematical lens model. Using the obtained geometry and optical power of the AIOL, the optimal AIOL may be chosen from a set of variously sized lenses 912 or custom manufactured using a conventional IOL manufacturing system 914, and finely adjusted as described above.

The processing device 906 may be implemented by computer-executable instructions, such as program modules, that are executed by a conventional computer. Generally, program modules include routines, programs, objects, components, data structures, etc. that performs particular tasks or implement particular abstract data types. Those skilled in the art will appreciate that the invention may be practiced with various computer system configurations, including multi-processor systems, microprocessor-based or programmable consumer electronics, minicomputers, mainframe computers, and the like. The invention may also be practiced in distributed computing environments where geometric parameters are measured by remote measuring devices that are linked through a communications network. In a distributed computing environment, program modules may be located in both local and remote computer-storage media including memory storage devices.

Any suitable programming language may be used to implement without undue experimentation the analytical functions described above. Illustratively, the programming language used may include assembly language, Ada, APL, Basic, C, C++, C*, COBOL, dBase, Forth, FORTRAN, Java, Modula-2, Pascal, Prolog, Python, REXX, and/or JavaScript for example. Further, it is not necessary that a single type of instruction or programming language be utilized in conjunction with the operation of the system and method of the invention. Rather, any number of different programming languages may be utilized as is necessary or desirable.

The computing environment may also include other removable/nonremovable, volatile/nonvolatile computer storage media. For example, a hard disk drive may read or write to nonremovable, nonvolatile magnetic media. A magnetic disk drive may read from or writes to a removable, nonvolatile magnetic disk, and an optical disk drive may read from or write to a removable, nonvolatile optical disk such as a CD-ROM or other optical media.

The processor that executes commands and instructions may be a general-purpose processor, but may utilize any of a wide variety of other technologies including special-purpose hardware, a microcomputer, mini-computer, mainframe computer, programmed micro-processor, micro-controller, peripheral integrated circuit element, a CSIC (Customer Specific Integrated Circuit), ASIC (Application Specific Integrated Circuit), a logic circuit, a digital signal processor, a programmable logic device such as an FPGA (Field Programmable Gate Array), PLD (Programmable Logic Device), PLA (Programmable Logic Array), RFID processor, smart chip, or any other device or arrangement of devices that is capable of implementing the steps of the processes of the invention.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. A method for customizing geometry and a focusing power of a fluid-filled intraocular lens comprising a shell to provide both distance and near vision correction for a patient, the method comprising:
   a. determining a baseline amount of far-field focal correction for the patient;
   b. measuring at least one accommodation-related parameter for the patient;
   c. estimating at least one accommodation-related parameter for the patient based at least in part on statistical data;
   d. predicting an accommodative amplitude based on the measured and estimated accommodation-related parameters; and
   e. determining the intraocular lens geometry and a fill volume and an optical property of the filling fluid contained in the intraocular lens for providing a desired focusing power and accommodative level based at least in part on (i) the baseline correction, (ii) the predicted accommodative amplitude, (iii) a first relationship between the fill volume of the filling fluid and a lens pressure exerted by the filling fluid on the shell, and (iv) a second relationship between the accommodative level and the lens pressure exerted on the shell.

2. The method of claim 1 wherein the estimated accommodation-related parameters comprise at least one of a demographic characteristic, a behavioral characteristic, or a medical history.

3. The method of claim 1 wherein the intraocular lens geometry and power is further determined based on a mathematical model.

4. The method of claim 1 wherein the at least one measured accommodation-related parameter is one or more of corneal topography, corneal keratometry, conical aberration, axial eye length, anatomic geometry of the natural lens and or lens capsule including lens or lens capsule volume, diameter, thickness, or curvature, geometry of ciliary muscles in a relaxed and contracted position, or the position of the tens and lens capsule relative to the eye.

5. The method of claim 1 further comprising choosing an optimal lens from among a plurality of differently sized lenses based on the determined geometry and power.

6. The method of claim 1 further comprising manufacturing an intraocular lens based on the determined geometry.

7. The method of claim 1 further comprising adjusting at least one of the fill volume or the optical property of the filling fluid contained in the intraocular lens for maximizing a working focal range of the lens.

8. The method of claim 1 further comprising the steps of:
   a. predicting an accommodated lens power; and
   b. selecting a base power of the intraocular lens based at least in part on the difference between the predicted accommodated lens power and the predicted accommodative amplitude.

9. The method of claim 8 further comprising setting the base power and the accommodative amplitude to ensure that the intraocular lens encompasses both distance vision and near vision.

10. The method of claim 1 further comprising:
    estimating (i) a force applied to the intraocular lens by a lens capsule based on the measured and estimated accommodation-related parameters, (ii) a pressure inside the intraocular lens, and (iii) at least one parameter relating to the shell of the intraocular lens; and
predicting the accommodative amplitude based at least in part on the estimated force, pressure, and the at least one parameter relating to the shell.

11. The method of claim 10 wherein the accommodative amplitude is further determined based on a mathematical model.

12. A system for customizing geometry and a focusing power of a fluid-filled intraocular lens comprising a shell to provide both distance and near vision correction for a patient, the system comprising:
a measuring system for (a) determining a baseline amount of far-field focal correction for the patient and (b) measuring at least one accommodation-related parameter for the patient;
a memory for storing a database comprising accommodation-related statistical data; and
a processor in operative communication with the measuring system and the memory, the processor being configured to (a) estimate at least one accommodation-related parameter for the patient based at least in part on statistical data; (b) predict an accommodative amplitude based on the measured and estimated accommodation-related parameters; and (c) determine the intraocular lens geometry and a fill volume and an optical property of the filling fluid contained in the intraocular lens for providing a desired focusing power and accommodative level based at least in part on (i) the baseline correction, (ii) the predicted accommodative amplitude, (iii) a first relationship between the fill volume of the filling fluid and a lens pressure exerted by the filling fluid on the shell, and (iv) a second relationship between the accommodative level and the lens pressure exerted on the shell.

13. The system of claim 12 wherein the processor is further configured to determine the intraocular lens geometry and power based on a mathematical model.

14. The system of claim 12 wherein the measuring system measures at least one of corneal topography, corneal keratometry, corneal aberration, axial eye length, anatomic geometry of the natural lens and or lens capsule including lens or lens capsule volume, diameter, thickness, or curvature, geometry of ciliary muscles in a relaxed and contracted position, or the position of the lens and lens capsule relative to the eye.

15. The system of claim 12 wherein the database stores statistical data on at least one of a demographic characteristic, a behavioral characteristic or a medical history.

16. The system of claim 12 wherein the processor is further configured to choose an optimal lens from among a plurality of differently sized lenses based on the determined geometry and power.

17. The system of claim 12 wherein the processor is further configured to communicate with a manufacturing system for manufacturing the intraocular lens based on the determined geometry and power.

18. The system of claim 12 wherein the processor is further configured to compute an adjustment to at least one of the refill volume or the optical property of the filling fluid contained in the intraocular lens for optimizing distance and near vision correction.

19. The system of claim 12 wherein the processor is further configured to:
a. predict an accommodated lens power; and
b. predict a base power of the intraocular lens based at least in part on the difference between the predicted accommodated lens power and the predicted accommodative amplitude.

20. The system of claim 19 wherein the processor is further configured to set the base power and the accommodative amplitude to ensure that the intraocular lens encompasses both distance vision and near vision.

21. The system of claim 12 wherein the measuring system comprises at least one of a keratometer, a wavefront aberrometer, an IOL Master, a corneal topographer, ultrasound or optical coherence tomography, a Scheimpflug camera, a magnetic resonance imaging device, a computed tomography device, or an intraoperative aberrometer.

22. The system of claim 12 wherein the processor is further configured to;
estimate (i) a force applied to the intraocular lens by a lens capsule based on the measured and estimated accommodation-related parameters, (ii) a pressure inside the intraocular lens, and (iii) at least one parameter relating to the shell of the intraocular lens; and
predict the accommodative amplitude based at least in part on the estimated force, pressure, and the at least one parameter relating to the shell.

23. The system of claim 12 wherein the processor is further configured to determine the accommodative amplitude based on a mathematical model.

24. The method of claim 1 wherein the accommodative level positively correlates with the fill volume of the filling fluid.

* * * * *

UNITED STATES PATENT AND TRADEMARK OFFICE
CERTIFICATE OF CORRECTION

PATENT NO. : 9,433,497 B2  
APPLICATION NO. : 14/058634  
DATED : September 6, 2016  
INVENTOR(S) : Charles DeBoer et al.

Page 1 of 1

It is certified that error appears in the above-identified patent and that said Letters Patent is hereby corrected as shown below:

In Claim 4, Column 16, Line 44, change "tens" to --lens--.

Signed and Sealed this  
Twenty-first Day of February, 2017

Michelle K. Lee  
*Director of the United States Patent and Trademark Office*